United States Patent [19]

Tuinstra et al.

[11] Patent Number: 5,189,139
[45] Date of Patent: Feb. 23, 1993

[54] PREPARATION OF POLYCARBONATES COMPRISING SEPARATING BISPHENOL, CONVERTING BISPHENOL TO DIARYL CARBONATE AND RECYCLING

[75] Inventors: Hendrik E. Tuinstra; Harold D. Myers, both of Midland, Mich.

[73] Assignee: The Dow Chemical Company, Midland, Mich.

[21] Appl. No.: 741,925

[22] Filed: Aug. 8, 1991

[51] Int. Cl.⁵ .............................................. C08G 64/24
[52] U.S. Cl. ...................................... 528/196; 526/67; 526/68; 528/198; 528/502
[58] Field of Search ....................... 528/196, 198, 502; 526/67, 68

[56] References Cited

U.S. PATENT DOCUMENTS 4,452,968  6/1984  Bolon et al. ......................... 528/371

Primary Examiner—Harold D. Anderson

[57] ABSTRACT

A process for the preparation of a polycarbonate comprising reacting a diaryl carbonate with a bisphenol to produce a polycarbonate and a phenol, regenerating the diaryl carbonate by reacting the phenol byproduct with a carbonyl halide, and optionally recycling the hydrogen halide using a metal Redox captive halogen swing reactor system.

4 Claims, 1 Drawing Sheet

PREPARATION OF POLYCARBONATES COMPRISING SEPARATING BISPHENOL, CONVERTING BISPHENOL TO DIARYL CARBONATE AND RECYCLING

BACKGROUND OF THE INVENTION

The present invention relates to a process for te preparation of polycarbonates. More particularly, the present invention allows for the preparation of polycarbonates via an integrated process utilizing as reactants a bisphenol and phosgene.

In U.S. Pat. No. 4,452,968 an integrated process for the preparation of aromatic polycarbonates was disclosed wherein a methyl acetate by-product formed in the transesterification of a bisphenol diacetate with a dialkyl carbonate was recycled by heating the alkyl ester to form a ketene and subsequently such ketene was reconverted by reaction with a bisphenol to form additional quantities of the bisphenol diacetate. For the teachings contained therein the above identified patent is incorporated herein by reference thereto.

Preparation of a ketene intermediate has proven costly and inefficient due to the high temperatures involved and the fact that a dialkyl carbonate intermediate is formed in the process. Recoveries on the order of only about 80% of theoretical or less are typical, leading to the need to develop a more efficient means of generating polycarbonate resins.

Another integrated process for preparing polycarbonates is disclosed in U.S. Pat. No. 4,954,613. In this process a dialkyl carbonate is reacted with a bisphenol dicarboxylate to prepare the polycarbonate oligomer. The alkyl ester byproduct is carbonylated to form an anhydride, typically acetic anhydride, which is reacted with a bisphenol to regenerate the bisphenol dicarboxylate. This step liberates a coproduct carboxylic acid, typically acetic acid.

The generation of the coproduct is undesired since the process requires either use or disposal of the coproduct. Often the coproduct must be purified before use or sale thereby adding further complexity and cost to the total process. In practice the producer is rarely able to maximize recovered costs since the byproduct volumes are determined in fixed ratio to generation of the desired product and not according to a separate marketing plan.

SUMMARY OF THE INVENTION

According to the present invention, there is now provided a process for producing a bisphenol polycarbonate comprising the steps of:
  A. reacting a diaryl carbonate with a bisphenol to produce a bisphenol polycarbonate and a phenol;
  B. separating the polycarbonate and phenol;
  C. reacting a carbonyl halide with at least some of the phenol from step B to produce a diaryl carbonate, and recycling the diaryl carbonate to step A.

DETAILED DESCRIPTION OF THE INVENTION

Figure 1:
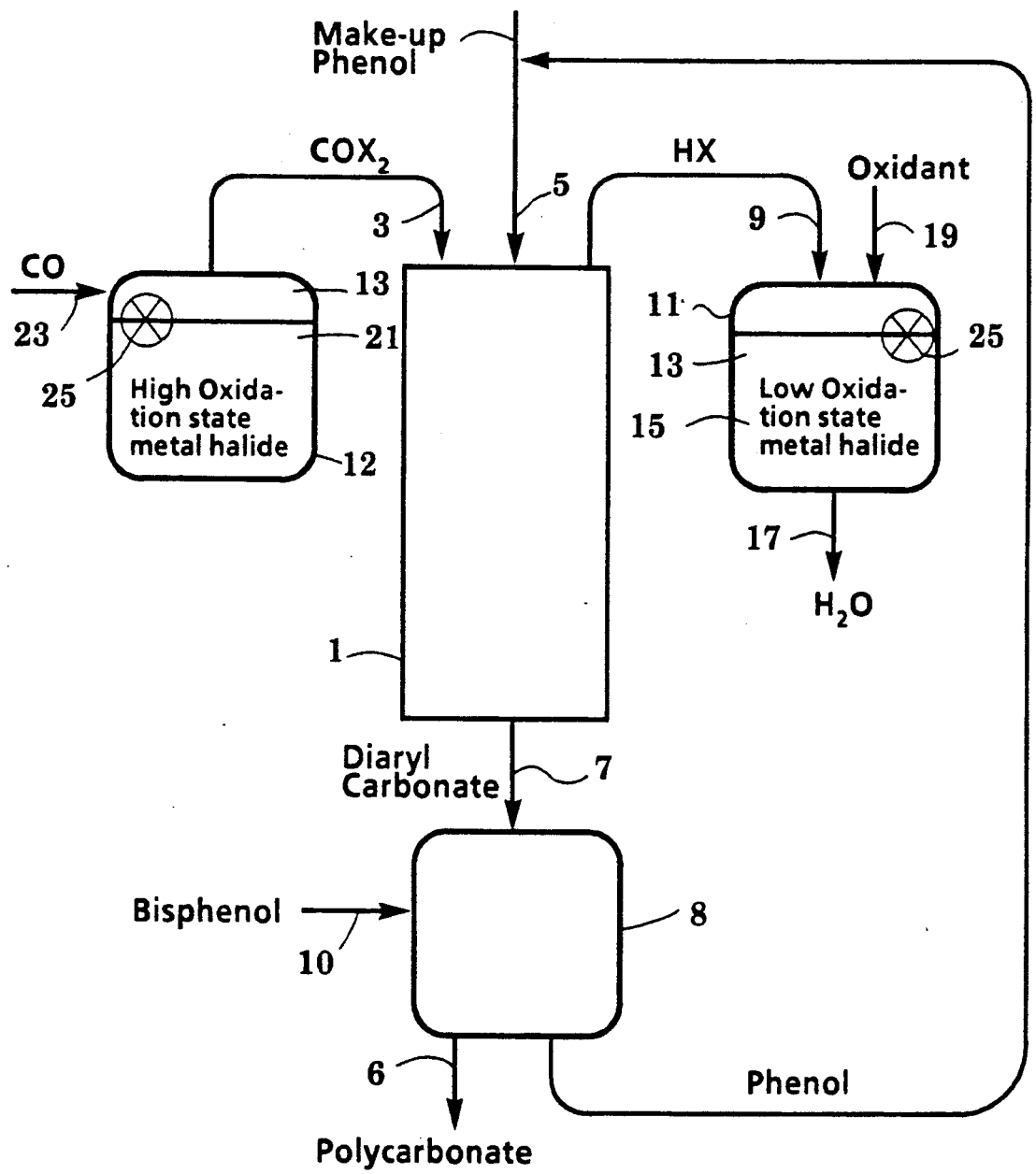

The reaction of bisphenols with a diaryl carbonate to form a polycarbonate and a phenol, step A of the present invention, is a well known reaction. Suitable process conditions are disclosed for example in U.S. Pat. No. 3,888,826, the teachings of which are incorporated herein by reference thereto. By the term bisphenol is meant dihydroxy aromatic compounds as well as inertly substituted dihydroxy aromatic compounds. Examples of suitable bisphenol reactants include bisphenol-A, bisphenol-F, bisphenol-K, dihydroxy biphenyl, and halo, or $C_{1-6}$ alkyl substituted derivatives of the foregoing. In schematic form, the reaction of a bisphenol and a diarylcarbonate may be depicted by the following illustration:

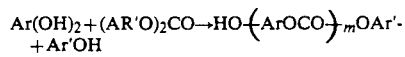

wherein Ar represents a bisphenol remnant formed by removal of two hydroxyl groups therefrom, and Ar' represents a phenol remnant formed by removal of the hydroxyl group therefrom.

Suitable catalysts for the transesterification reaction include alkali metal salts such as lithium hydroxide, lithium phenate, bisphenol-A dilithium, etc. Suitable temperatures for the reaction are from 150° to 380° C. The initial polycarbonate produced in accordance with transesterification step A is generally a relatively low molecular weight oligomer having from 5 to 15 repeating units. This low molecular weight prepolymer can be advanced to a higher molecular weight polymer by merely heating the prepolymer. Another technique for increasing polymer molecular weight, known as solid state advancement, utilizes prepolymer which has been converted to a crystalline state. This latter technique is disclosed in U.S. Pat. No. 4,948,871, the teachings of which are incorporated herein by reference. Both processes produce additional quantities of phenol which may be separated from the polymer and recycled to step C.

The separation of phenol and polycarbonate is relatively simple especially under the preferred operating conditions of the present invention where substantially no solvent is utilized. Generally the phenol is distilled from the mixture, optionally at reduced pressure to insure complete removal of phenol.

Any reaction conditions and catalysts known in the prior art for the reaction of a phenolic compound and a carbonyl halide may be suitably employed in step C. Examples include homogeneous metal phenate catalyzed processes such as those disclosed in U.S. Pat. No. 3,251,873; processes catalyzed by tetramethyl ammonium halides disclosed in U.S. Pat. No. 3,837,555; or processes catalyzed by aromatic heterocyclic basic nitrogen compounds, salts or adducts thereof disclosed in U.S. Pat. No. 4,012,406 and activated aromatic, N-containing heterocyclic or organophosphine catalyzed reactions disclosed in U.S. Ser. Nos. 451,893 and 451,894 filed Dec. 18, 1989, both now abandoned.

Heterogeneously catalyzed reactions may also be employed. Examples of suitable heterogeneously catalyzed reactions are processes using Lewis acids or transition metal compounds that generate Lewis acids, disclosed in U.S. Pat. No. 4,045,464. Another suitable process is the supported metal salt catalyzed process disclosed in U.S Ser. No. 429,954, now abandoned filed Oct. 30, 1989. A further suitable process utilizing $AlF_3$ catalysts is disclosed and claimed in the U.S. Ser. No., 706,426, filed May 28, 1991. The foregoing patents and pending applications are incorporated in their entireties herein by reference thereto.

Preferred carbonyl halides for use in the present process are phosgene, bromophosgene and mixtures thereof. A most preferred carbonyl halide is phosgene. Aryl haloformates, which may be thought of as the intermediate product resulting from reaction of a carbonyl halide and the phenolic compound may also be prepared by the process. They may be separated from the desired diaryl carbonate and recycled by contacting with the same or another phenolic compound in one embodiment of the present invention.

A desirable mole ratio of the phenolic compound to the carbonyl halide is 1:1 to 3:1. Higher ratios of carbonyl halide relative to the phenolic compound result in larger amounts of aryl haloformate being formed. Preferred molar ratios of phenolic compound to carbonyl halide are from 1.8:1 to 2.1:1.

As a general rule the reaction for step C employs temperatures from 25° C. to 450° C., preferably 100° C. to 130° C. The process is desirably carried out using phosgene under either liquid or gaseous reaction conditions. Pressures from about 0.01 atm to about 50 atm may be used, with pressures from about 0.1 atm to about 5 atm being preferred. Inert diluents such as nitrogen, toluene, carbon dioxide, etc. may also be present if desired.

Of the foregoing techniques for preparing diarylcarbonates, the preferred method uses homogeneous catalysts, especially $AlCl_3$, temperatures from 120° to 150° C., and no solvent, i.e. neat reaction conditions.

The process of step C can be carried out in any suitable reactor including a fixed bed reactor, a fluidized bed reactor or a circulating fluidized bed reactor, in which case the catalyst desirably is utilized as a fluidizable powder. Desirable residence times in such reactors are from 1 to 3000 seconds. Preferred residence times are 1 to 60 seconds. Most preferred are residence times of 1 to 10 seconds. Materials of construction must be resistant to the highly corrosive carbonyl halide. Suitable materials are glass, glass lined steel and Hastalloy ™.

For heterogeneous catalysts, periodic regeneration of the catalyst can improve the conversion rate of starting materials to product. Regeneration is accomplished by treating the catalyst with methanol or water at an elevated temperature in the range of about 400° C. to about 600° C.

A hydrogen halide byproduct is also formed in step C. This may be recycled, sold or utilized in other processes. In a preferred embodiment the hydrogen halide byproduct is reconverted to a carbonyl halide and reused in the process. One technique for this procedure uses metal Redox swing reactors or other suitable system to convert the hydrogen halide to halogen. In the metal Redox swing process, two reactors or two separate regions of a single reactor are employed to alternately convert the hydrogen halide produced from step C to a high oxidation state metal halide by contacting the same with a low oxidation state metal halide in the presence of an oxidant. Thereafter the high oxidation state metal halide is reacted with carbon monoxide to regenerate the low oxidation state metal halide and release carbonyl halide.

A preferred metal Redox pair for such a swing reactor system is the copper(I)/copper(II) chloride system. During the oxidation cycle copper(I) chloride is converted to copper(II) chloride by reaction with hydrogen chloride and an oxidant. Water is the sole byproduct of the reaction. The preferred oxidant is an oxygen containing gas, especially air. The preferred reaction conditions for converting the hydrogen halide to the corresponding high oxidation state metal halide are temperatures of 100° to 500° C. and pressures from atmospheric (100 kPA) to 10 atmospheres (1 MPa).

During the reduction cycle copper(II) chloride is converted to copper(I) chloride by reacting copper(II) chloride with carbon monoxide to form phosgene. The preferred reaction conditions for regenerating the low oxidation state metal halide are temperatures from 50° to 500° C. and pressures of carbon monoxide from atmospheric (100 kPA) to 10 atmospheres (1 MPa). The net reaction is the conversion of hydrogen halide and carbon monoxide to carbonyl halide and water.

It is desirable to detect the presence of oxidant in the product stream exiting the oxidation bed. For such purpose an oxygen sensor may be utilized such that upon sensing imminent break through of oxygen from the bed used for conversion of the metal from low oxidation state to high oxidation state, the direction of flow in the swing reactor is reversed. Alternatively a carbon monoxide detector at the exit of the reduction bed can be used to signal when to reverse the flow of the swing reactor.

The diaryl carbonate reactant for step A is regenerated by reacting the phenolic byproduct with a carbonyl halide according to any suitable procedure. The reaction is generally expedited by the use of a catalyst, particularly aluminum trichloride and the use of elevated temperatures and pressures.

This step of the process may be illustrated schematically by the following diagram:

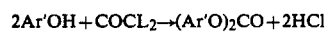

wherein Ar and Ar' are as previously defined.

Because of slight losses in the process it may be necessary to provide make-up quantities of the phenol. Preferably the phenol recycled from step B supplies at least 95 percent, more preferably at least 99 percent of the phenol reactant for step A.

The present process in its preferred embodiment wherein hydrogen halide is also recycled comprises the steps of:

A. reacting a diaryl carbonate with a bisphenol to produce a bisphenol polycarbonate and a phenol;
B. separating the polycarbonate and phenol;
C'. reacting a carbonyl halide with at least some of the phenol from step B to produce a hydrogen halide and a diaryl carbonate, and recycling the diaryl carbonate to step A;
D. contacting at least some of the hydrogen halide produced in step C' with a low oxidation state metal halide and an oxidant to generate water and the corresponding high oxidation state metal halide;
E. on or before exhaustion of the low oxidation state metal halide, contacting carbon monoxide with the high oxidation state metal halide formed in step D to generate carbonyl halide and regenerate the low oxidation state metal halide; and
F. recycling at least a portion of the carbonyl halide formed in step E for use in step C'.

The use of such a metal Redox swing system to recycle hydrogen halide in an integrated process to prepare polycarbonate resins is further illustrated by reference to FIG. 1 where there is illustrated a dual stage reactor system comprising the primary diaryl carbonate reactor 1, supplied with carbonyl halide via line 3. Diaryl carbonate product from step C' is removed to polymerization reactor 8, via line 7, and phenol byproduct from step A is removed via line 5 and supplied with necessary make-up phenol to primary reactor 1. Bisphenol is supplied to polymerization reactor 8, via line 10. The desired polycarbonate is removed via line 6, and may be further advanced to higher molecular weight if desired. Hydrogen halide product from step C' is routed via line 9, to one of two swing reactors, 11 and 12. Inside the reactor 11, is a layer 13 that absorbs oxygen and the low oxidation state metal halide layer 15. The hydrogen halide passes through layer 13 without reaction and reacts in the presence of a suitable oxidant with the low oxidation state metal halide forming a high oxidation state metal halide. and releasing water which is discharged via line 17. The oxidant is supplied via line 19. At the same time, swing reactor 12 is operating in the reduction mode. Carbon monoxide is supplied via line 23 and reacts with the high oxidation state metal halide to yield carbonyl halide and a low oxidation state metal halide. The carbonyl halide is discharged to the primary reactor via line 3. An oxygen sensor 25, placed slightly before the interface of the metal halide and absorbent layers detects imminent break through of oxygen indicating the need to reverse the direction of flow in the system. The layer, 13, is capable of absorbing oxidant should a slight break through into the layer occur.

After reversal, the operation of the twin swing reactors changes. The reactor that before had converted hydrogen halide is regenerated while supplying carbonyl halide to the primary reactor, and vice versa.

It may be readily observed that the present system allows for the overall conversion of a bisphenol to the corresponding polycarbonate utilizing a carbonyl halide. If desired byproduct hydrogen halide can be reconverted to carbonyl halide using carbon monoxide and oxygen reactants. This essentially eliminates the requirement of purchasing, storing, handling and using halogen for the preparation of carbonyl halides for use in the production of polycarbonates. The recycle of phenol and optional captive use of hydrogen halide and carbonyl chloride allows for great economy and simplicity in the resulting process.

In a further preferred embodiment of the invention, substantially no solvents other than the recited reactants are utilized in the various steps. In particular the polymerization is conducted under molten conditions such that no solvent needs to be separated from the phenol byproduct. Also no liquid/aqueous waste products are produced as in the conventional solution or interfacial processes for the production of polycarbonates. This allows for a process with significantly improved environmental impact.

What is claimed is:

1. A process for producing a polycarbonate comprising the steps of:
   A. reacting a diaryl carbonate with a bisphenol to produce a bisphenol polycarbonate and a phenol;
   b. separating the polycarbonate and phenol;
   C. reacting a carbonyl halide with at least some of the phenol from step B to produce a diaryl carbonate, and recycling the diaryl carbonate to step A.

2. A process according to claim 1 wherein the bisphenol is bisphenol A, the diaryl carbonate is diphenyl carbonate and the phenol is hydroxybenzene.

3. A process according to claim 1 wherein the carbonyl halide is phosgene.

4. A process according to claim 2 wherein the carbonyl halide is phosgene.

* * * * *